(12) United States Patent
Surti

(10) Patent No.: US 8,496,578 B2
(45) Date of Patent: Jul. 30, 2013

(54) ENDOSCOPIC BARREL WITH CONNECTOR

(75) Inventor: Vihar C. Surti, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 980 days.

(21) Appl. No.: 12/100,571

(22) Filed: Apr. 10, 2008

(65) Prior Publication Data

US 2008/0255412 A1     Oct. 16, 2008

Related U.S. Application Data

(60) Provisional application No. 60/923,410, filed on Apr. 13, 2007.

(51) Int. Cl.
*A61B 17/10* (2006.01)
*A61B 1/00* (2006.01)
*A61B 1/06* (2006.01)

(52) U.S. Cl.
USPC ............ 600/127; 606/139; 606/140; 606/141

(58) Field of Classification Search
USPC .................................. 600/127; 606/139–150
See application file for complete search history.

(56) References Cited

U.S. PATENT DOCUMENTS

| | | | |
|---|---|---|---|
| 3,555,171 A * | 1/1971 | Larson ........................ | 174/138 F |
| 4,706,653 A * | 11/1987 | Yamamoto .................... | 600/175 |
| 5,282,811 A | 2/1994 | Booker et al. | |
| 5,380,302 A | 1/1995 | Orth | |
| 5,624,453 A | 4/1997 | Ahmed | |
| 5,735,861 A | 4/1998 | Peifer et al. | |
| 6,007,551 A | 12/1999 | Peifer et al. | |
| 6,059,797 A * | 5/2000 | Mears ........................... | 606/140 |
| 6,074,402 A | 6/2000 | Peifer et al. | |
| 6,565,578 B1 | 5/2003 | Peifer et al. | |
| 6,730,101 B1 * | 5/2004 | Peifer et al. .................. | 606/140 |
| 6,974,466 B2 | 12/2005 | Ahmed et al. | |
| 7,125,283 B1 * | 10/2006 | Lin ............................... | 439/578 |

(Continued)

FOREIGN PATENT DOCUMENTS

| EP | 1 535 577 A1 | 6/2005 |
|---|---|---|
| WO | WO 97/16120 | 5/1997 |

OTHER PUBLICATIONS

International Search Report—PCT/US2008/059845 (Sep. 2, 2008).

*Primary Examiner* — Katherine Dowe
*Assistant Examiner* — Kevin G Barry, III
(74) *Attorney, Agent, or Firm* — Brinks Hofer Gilson & Lione

(57) ABSTRACT

An endoscopic assembly for an endoscope is disclosed. The assembly comprises a ligator barrel having proximal and distal portions. The proximal portion has a seat and a receiving wall extending to a proximal end. The receiving wall has a first threaded portion formed thereon. The assembly further comprises a connector for connecting the ligator barrel about the endoscope. The connector has a scope portion and a tip portion. The scope portion has a receiving end through which the endoscope is disposed to engage the seat for connecting the ligator barrel about the endoscope. The tip portion has a second threaded portion formed thereon and are configured to cooperate with the first threaded portion to receive the receiving wall and attach the connector with the ligator barrel. The first and second threaded portions are configured to cooperate with each other to tighten the connection of the ligator barrel about the endoscope as the threads increase surface area contact therebetween.

17 Claims, 3 Drawing Sheets

U.S. PATENT DOCUMENTS

| | | | |
|---|---|---|---|
| 7,189,247 B1 * | 3/2007 | Zirps et al. | 606/140 |
| 7,485,092 B1 * | 2/2009 | Stewart et al. | 600/127 |
| 2002/0195819 A1 * | 12/2002 | Sagaser | 285/249 |
| 2004/0006256 A1 * | 1/2004 | Suzuki et al. | 600/140 |

* cited by examiner

ENDOSCOPIC BARREL WITH CONNECTOR

CROSS-REFERENCE TO RELATED APPLICATIONS

This application claims the benefit of U.S. Provisional Application Ser. No. 60/923,410, filed on Apr. 13, 2007, entitled "ENDOSCOPIC BARREL WITH CONNECTOR," the entire contents of which are incorporated herein by reference.

BACKGROUND OF THE INVENTION

The present invention relates to endoscopes, including endoscopic ligators, with universal connectors.

Endoscopic devices have been commonly used for various procedures, typically in the abdominal area. Endoscopy is the examination and inspection of the interior of body organs, joints or cavities through an endoscope. Endoscopy allows physicians to peer through the body's passageways. An endoscopic procedure may be used to diagnose various conditions by close examination of internal organ and body structures and may also guide therapy and repair, such as the removal of torn cartilage from the bearing surfaces of a joint.

The endoscopic treatment of lesions presently encompasses a variety of techniques such as electrocauterization, laser photocoagulation, heat therapy by the application of heat probes, and sclerotherapy which involves the injection of medicine into a target varix by a needle passed through the working channel of the endoscope. A further, widely used and increasingly promising technique involves the ligation of lesions, wherein mucosal and submucosal tissue is strangulated by an elastic ligature.

Generally, ligation involves applying a band or ligature around a portion of tissue, thereby cutting off blood or fluid flow and causing the tissue to necrose and separate from adjacent healthy tissue. It is widely used to treat a number of medical conditions, including, but not limited to, hemorrhoids, polyps, ballooning varices, and other types of lesions, including those that are cancerous. Various types of instrumentation have been developed that are capable of deploying one or more preloaded ligating bands with the emphasis being on minimally-invasive devices that can be introduced through a natural body opening. The two primary types of ligating band dispensers are those designed to fit over, or work within an endoscope for treating sites that cannot be viewed directly, and simpler, stand-alone devices designed for situations where use of a standard endoscope is not necessary or required. Typically, both types are used with a suction or vacuum means to draw the tissue into the distal tip, whereby the band is deployed over the base of the diseased tissue to cut off blood flow.

A number of instruments for effecting the ligation of body tissue by the application of an elastic ring have been used. Some of these instruments, because of their rigidity and size, are suited only for treatment of lesions that are in the external regions of the body or in the shallow body cavities. Others are particularly suited for the ligation of tissue in the abdominal cavity, such as for tubal ligation, when the abdominal cavity has been opened surgically.

In many instances, there are a number of different sized endoscopes for which a ligation treatment is used. A typical endoscopic ligation barrel may only accommodate one size of an outer diameter of an endoscope. Thus, for each different sized endoscope, a different accommodating-sized ligator barrel or tip is required, thereby further increasing the cost of endoscopy.

Thus, it is desirable to provide an assembly or device that is compatible with and accommodates various endoscope sizes.

BRIEF SUMMARY OF THE INVENTION

The present invention generally provides an assembly that is compatible with a number of endoscopes particularly but not necessarily for ligation. The assembly is relatively easy to use and accommodates various endoscope sizes.

In one embodiment, the assembly comprises a barrel having proximal and distal portions. The proximal portion has a seat and a receiving wall extending to a proximal end. The receiving wall has a first threaded portion formed thereon. The assembly further comprises a connector for connecting the barrel about the endoscope. The connector has a scope portion and a tip portion. The scope portion has a receiving end through which the endoscope is disposed to engage the seat for connecting the barrel about the endoscope. The tip portion has a second threaded portion formed thereon. The second threaded portion is configured to cooperate with the first threaded portion to receive the receiving wall and attach the connector and the barrel. The first and second threaded portions are configured to cooperate with each other to tighten the connection of the barrel about the endoscope as the threads increase surface area contact therebetween.

In another embodiment, the present invention provides an endoscope apparatus. In this embodiment, the apparatus comprises an endoscope assembly including an insertion tube having a distal end and a plurality of channels through which endoscopic parts may be disposed. The assembly further comprises a control system in mechanical and fluid communication with the insertion tube. The control system is configured to control at least one of the endoscopic parts. The apparatus further includes the endoscopic assembly disposed on the distal end of the insertion tube.

Further objects, features, and advantages of the present invention will become apparent from consideration of the following description and the appended claims when taken in connection with the accompanying drawings.

DETAILED DESCRIPTION OF THE INVENTION

The present invention generally provides an assembly that accommodates various endoscope sizes particularly, but not necessarily for ligation use. One embodiment of the present invention comprises a threaded hood (e.g., a threaded ligator barrel) and a threaded connector configured to cooperate with the threaded hood to receive various sizes of endoscopes particularly for ligation. In this embodiment, the threaded hood is a threaded ligator barrel. An endoscope is disposed through the connector and engages the ligator barrel. Cooperation between the ligator barrel and the connector tightens about the endoscope. In one embodiment, a gasket is disposed within the barrel and is collapsible when the ligator barrel and the connector cooperate with each other. As the ligator barrel is turned or screwed on the connector, the gasket tightens about the endoscope. The degree of turns depends on the size of the outer diameter of the endoscope.

Figure 1:
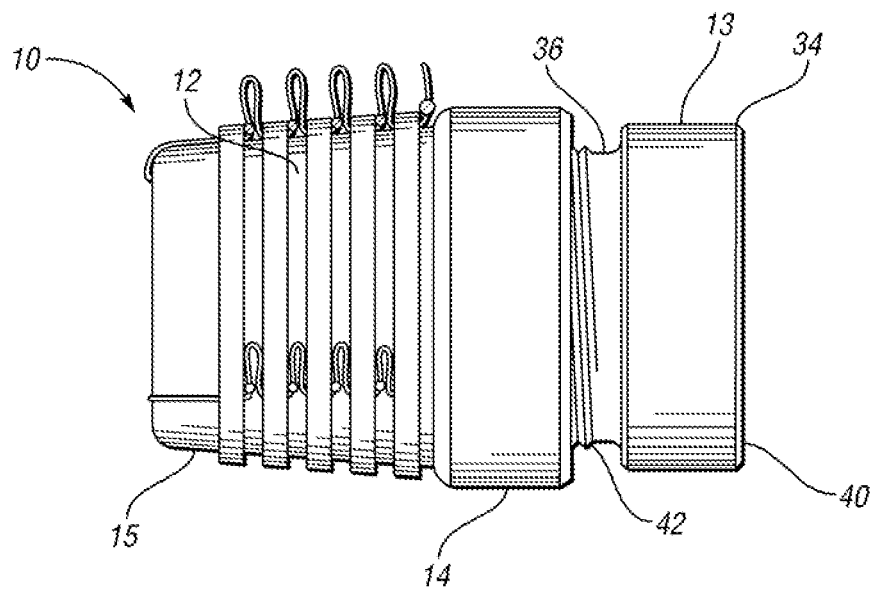
FIG. 1 is a side view of an assembly in accordance with one embodiment of the present invention.
Figure 2:
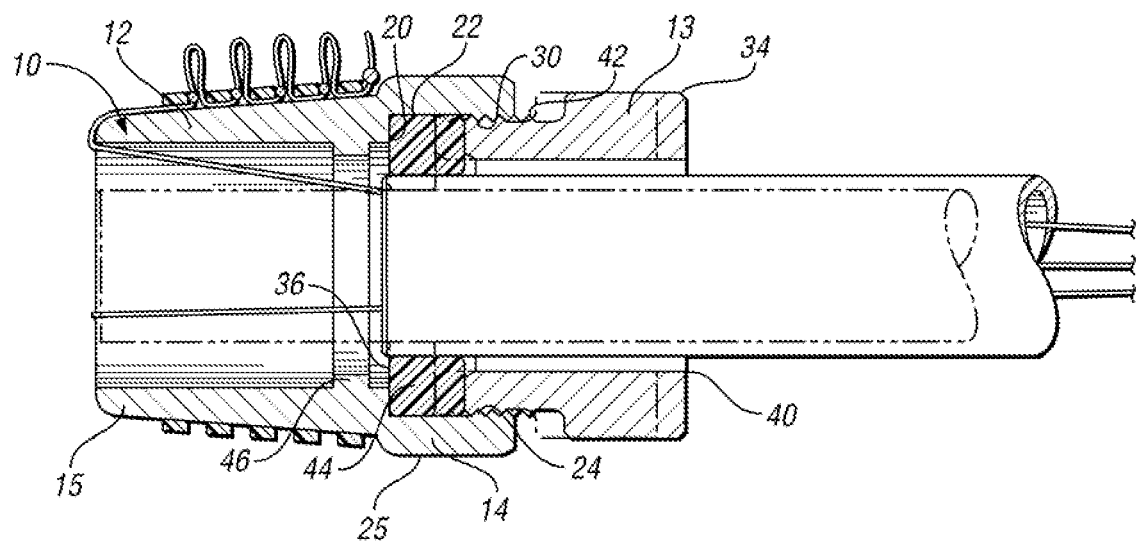
FIG. 2 is a cross-sectional side view of the assembly configured to receive a distal end of an endoscope.

FIGS. 1 and 2 illustrate an endoscopic assembly 10 for an endoscope in accordance with one embodiment of the present invention. As shown, the assembly 10 comprises a threaded hood 12, e.g. a threaded ligator barrel, having proximal and distal portions 14, 15. In this embodiment the threaded hood is a threaded ligator barrel 12 for ligation. For example, the endoscopic assembly may be used for the ligation of lesions.

Each of the proximal and distal portions 14, 15 has an inner diameter formed therethrough. In this embodiment, the inner diameter of the distal portion 15 is less than the inner diameter of the proximal portion 14 thereby defining a seat 20 of the hood 12. That is, the hood 12 comprises a step change between the inner diameters of the proximal and distal portions 14, 15 to define the seat 20 of the hood 12. In this embodiment, the proximal portion 14 includes the seat 20 and a receiving wall 22 that extends therefrom to a proximal end 23. As shown, the receiving wall 22 comprises inner and outer surfaces 24, 25. The receiving wall 22 further comprises a first threaded portion 30 formed on the inner surface 24 of the receiving wall 22. Alternatively, the first threaded portion 30 may be formed on the outer surface 25 of the receiving wall 22 without falling beyond the scope or spirit of the present invention.

In this embodiment, the distal portion 15 comprises a stop 46 radially formed about its inner diameter and extending inwardly. As will be described in greater detail below, the stop 46 functions to prevent distal advancement of the endoscope relative to the assembly. The hood 12 further comprises a gasket 44 disposed on the seat 20 within the receiving wall 22 of the hood 12. Preferably, the gasket 44 comprises an inner diameter that is less than the inner diameter of the distal portion 15 of the hood 12. In this embodiment, the gasket 44 engages the receiving wall 22 and is configured to receive various sizes of endoscopes for ligation.

As mentioned, the assembly is compatible with different-sized endoscopes particularly but not necessarily for ligation use. In one embodiment, the assembly may be configured to cooperate with endoscope distal tips having an outer diameter range of between about 5 millimeters (mm) and 16 mm. For example, a connector having an outer diameter of about 11 mm and an inner diameter of slightly greater than 9 mm may receive an endoscope distal tip having an outer diameter of about 9 mm. In this example, the hood may have an outer diameter of about 12 mm and an inner diameter of slightly greater than 11 mm to receive the connector. The gasket may have an inner diameter of about 9.5 mm. Of course, other sizes may be used without falling beyond the scope or spirit of the present invention.

In this embodiment, the hood 12 is transparent so that an endoscope may insert therethrough and allow a clinician to view a desired location within a body cavity. In one embodiment, the ligator is made of any suitable material such as a clear polymer, e.g., polycarbonate or polyurethane. For example, the assembly 10 may be implemented for the following procedures: ligation with an endoscope during gastroscopy, sigmoidoscopy and colonoscopy, esophago gastro duodenoscopy (EGD), endoscopic retrograde cholangiopancreatography (ERCP), and bronchoscopy.

As illustrated in FIGS. 1 and 2, the endoscopic assembly 10 further comprises a connector 13 for connecting the hood 12 about an endoscope in accordance with one embodiment of the present invention. As shown, the connector 13 has a scope portion 34 and a tip portion 36 extending from the scope portion 34. In this embodiment, the scope portion 34 has a receiving end 40 through which an endoscope may be disposed. The gasket 44, disposed in the ligation barrel 12, is configured to receive the endoscope and allow the endoscope to engage the seat 20 of the hood 12, thereby connecting the hood 12 about the endoscope. As shown, the tip portion 36 comprises inner and outer surfaces 37, 38. The tip portion 36 has a second threaded portion 42 formed on the outer surface 38. However it is to be noted that the second threaded portion 42 may be formed on the inner surface 24 of the connector 32 so long as the first threaded portion 30 are formed about the outer surface 25 of the receiving wall 22.

Preferably, the second threaded portion 42 is configured to cooperate with the first threaded portion 30 and receive the receiving wall 22 to attach the connector 13 and the hood 12. In use, the first and second threaded portion cooperate with each other to tighten the connection of the hood 12 about the endoscope as the threads increase surface area contact therebetween. The gasket 44 is configured to collapse when the first threaded portion 30 engages with the second threaded portion 42. The cooperation of the threads reduce the inner diameter of the gasket 44 to press fit about the endoscope. Thus, as the first and second threaded portions engage and are "screwed" or turned together, the inside diameter of the gasket 44 collapses, thereby tightening the grip about the endoscope disposed therethrough. As the hood 12 is turned or screwed on the connector 13, the gasket 44 tightens about the endoscope. The degree of turns depends on the size of the outer diameter of the endoscope. Furthermore, the stop 46 has an inner diameter that effectively prevents an endoscope from distally advancing further into the distal portion of the barrel 12.

Figure 3:
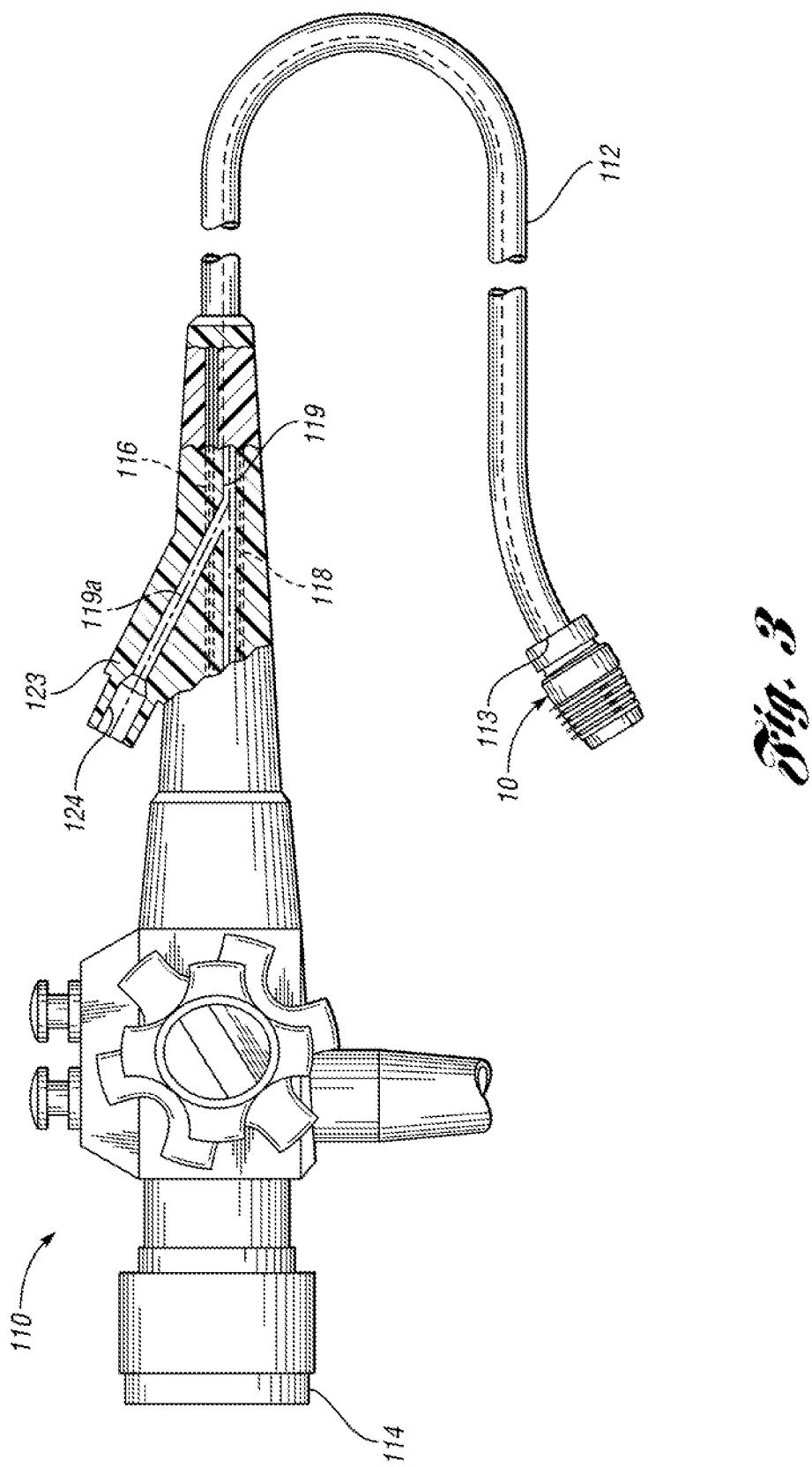
FIG. 3 is a side view of an endoscope apparatus implementing the assembly in accordance with one embodiment of the present invention.

FIG. 3 illustrates a flexible endoscopic apparatus or instrument 110 comprising the ligation assembly 10 in accordance with one embodiment of the present invention. The apparatus 110 has a length that permits access to the deeper regions of a hollow body organ. In certain embodiments, the flexible apparatus 110 can be sized for insertion into the alimentary tract. In accordance with one embodiment, the apparatus 110 includes a conventional endoscope with an operating control section 111 and an insertion tube or a flexible section 112 that terminates at a distal insertion end 113. The operating control section 111 includes a viewing end 114 remote from the insertion end 113, through which a ligating procedure can be directly observed.

It is to be understood that any other suitable endoscopic apparatus may be used with the assembly described above. For example, various endoscopic ligating apparatus may be used including but not limited to U.S. Pat. No. 6,007,551 entitled "Endoscopic Ligating Apparatus" filed on Sep. 6, 1996 and U.S. Pat. No. 5,624,453 entitled "Endoscopic Ligating Instrument" filed on Oct. 30, 1995, the entire contents of each are incorporated herein by reference.

Figure 5:
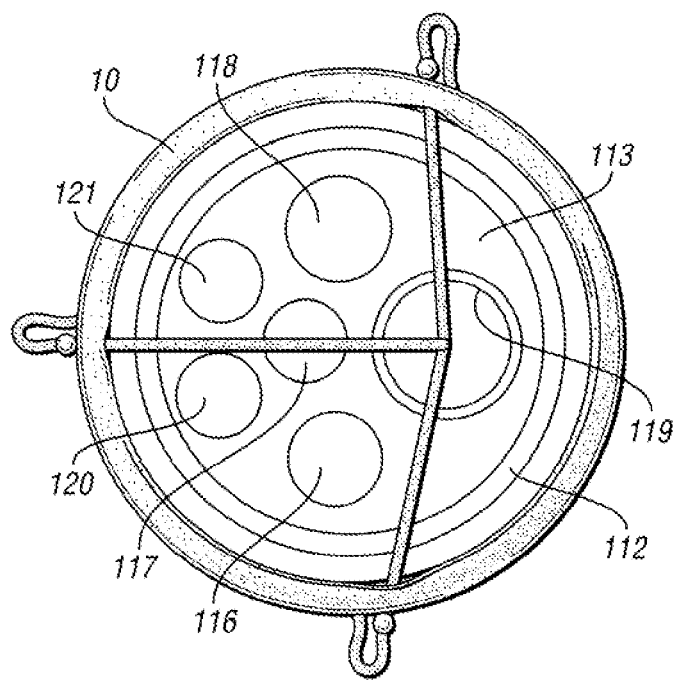
FIG. 5 is an end view of the endoscope apparatus of FIG. 4.

Referring to FIGS. 3 and 5, the endoscopic instrument 110 may include a plurality of channels extending from the operating control section 111 and through the flexible section 112 to the insertion end 113. For example, the instrument 110 can include an illumination channel 116 through which a fiberoptic cable is inserted for the transmission of light from a light source. A viewing channel 117 can also be provided with a fiberoptic cable for viewing purposes, while a third channel 118 can be provided for application of suction at the surgical site. The endoscopic instrument 110 can also include a working channel 119 through which a plurality of tools and instruments can be extended, an irrigation channel 120 to allow delivery of fluid to the ligation site, and an air channel 121 that can be used to deliver pressurized air, such as for cleaning the lens at the insertion end of the viewing channel 117.

In one embodiment, the endoscopic instrument 110 also includes an auxiliary port portion 123 having a proximal opening 124. The working channel 119 extends into the auxiliary port 123 by way of a working channel extension 119a. Each of the channels preferably opens at the distal or insertion end 113 of the flexible section 112 of the endoscopic instrument 110.

The endoscope forming part of the instrument 110 of FIG. 3 can be of many different types. For example, the endoscope can be of the type commercially provided by Olympus, Pentax, or Fujinon. While most of the working components of these endoscopes are similar, each may have a different configuration for the proximal opening and the auxiliary port. Each of these specifically identified endoscopes, and other commercially available endoscopes, utilize different sealing members (not shown) at the proximal opening of the auxiliary port. It is understood that the various aspects of the present invention accommodate the secure attachment to various configurations and dimensions of a variety of endoscopes.

Figure 4:
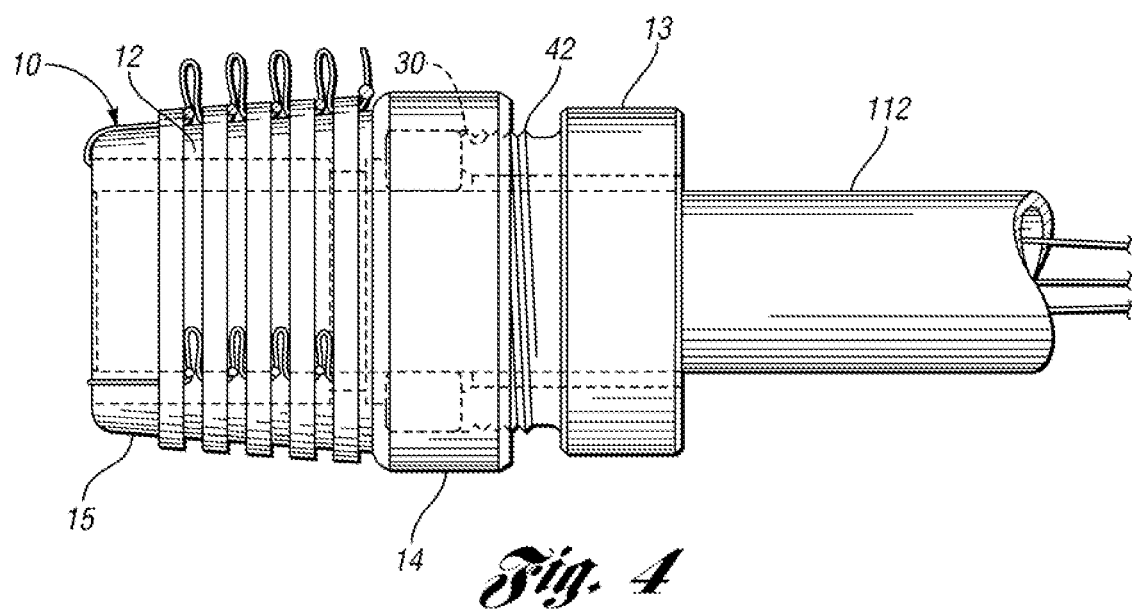
FIG. 4 is an enlarged view of the endoscope apparatus of FIG. 3 depicting the assembly.

Referring now to FIG. 4, details of the endoscopic assembly 10 can be discerned. In this embodiment, assembly 10 is disposed at the insertion end 113 of the flexible section 112 of the endoscope. The material of the hood or ligator barrel should be sufficiently strong or rigid to support a plurality of ligating bands or rings stretched onto the outer surface of the barrel. The ligating bands are typically formed of an elastic material, preferably a rubber material, or an inert non-toxic plastic composition.

The ligator barrel is preferably removably mountable to the insertion end 113 of the flexible endoscope section 112. In this manner, barrels pre-loaded with ligating bands or rings can be made available for mounting on the endoscope.

In use, the endoscopic assembly is preferably provided separately from the endoscopic instrument with the connector already mounted about the outer surface of the barrel. At an appropriate time in the use of the flexible endoscopic ligation instrument, the assembly can be mounted about the cylindrical surface of the flexible endoscope section by screwing or cooperating the first and second threaded portions together. The endoscopic assembly allows for a range of endoscope sizes cooperable with the assembly. Depending on the outer diameter size of the endoscope, the threads of ligator barrel and the connector may cooperate to collapse the gasket over the endoscope accordingly.

Further description of ligating apparatus may be found in U.S. Pat. No. 6,007,551 entitled "ENDOSCOPIC LIGATING APPARATUS" issued on Dec. 28, 1999 and U.S. Pat. No. 5,624,453 entitled "ENDOSCOPIC LIGATING INSTRUMENT" issued on Apr. 29, 1997, the entire contents of each are incorporated herein by reference.

While the present invention has been described in terms of preferred embodiments, it will be understood, of course, that the invention is not limited thereto since modifications may be made to those skilled in the art, particularly in light of the foregoing teachings.

The invention claimed is:

1. An endoscopic assembly for an endoscope that has an outer diameter, the assembly comprising:
   a barrel having proximal and distal portions, the proximal portion having a radially extending seat and a circumferential receiving wall extending to a proximal end, the receiving wall having a first threaded portion formed thereon;
   a gasket having a distal surface disposed on the seat and a radially outer surface disposed on the receiving wall of the barrel and engaging the receiving wall, the gasket having an inner diameter configured to receive the endoscope; and
   a connector for connecting the barrel about the endoscope, the connector having a scope portion and a tip portion, the scope portion having a receiving end through which the endoscope is disposed to engage the seat for connecting the barrel about the endoscope, the tip portion having a second threaded portion formed thereon, the second threaded portion being configured to cooperate with the first threaded portion to receive the receiving wall and attach the connector with the barrel, the first and second threaded portions being configured to cooperate with each other to tighten the connection of the barrel about the endoscope as the threads increase surface area contact therebetween, the tip portion further having a tip end abutting the gasket on a proximal surface of the gasket, the endoscopic assembly being configured to axially compress the gasket between the seat and the tip end during tightening of the connection, thereby reducing the inner diameter of the gasket to press fit onto the endoscope if the outer diameter has any of a plurality of different values that are each within the range of between about 5 to 16 millimeters.

2. The assembly of claim 1 wherein the endoscope has an outer diameter, and wherein the surface area contact between the first and second threaded portions needed to tighten the connection depends on the outer diameter.

3. The assembly of claim 1 wherein the barrel comprises a stop radially formed therein and extends inwardly, preventing distal advancement of the endoscope relative to the assembly.

4. The assembly of claim 1 wherein the barrel is transparent.

5. The assembly of claim 1 wherein the barrel is made of clear polymer.

6. The assembly of claim 1 wherein the receiving wall comprises an inner surface having the first threaded portion formed thereon.

7. The assembly of claim 6 wherein the tip portion of the connector comprises an outer surface having the second threaded portion formed thereon.

8. The assembly of claim 1 wherein the receiving wall comprises an outer surface having the first threaded portion formed thereon.

9. The assembly of claim 8 wherein the tip portion of the connector comprises an inner surface having the second threaded portion formed thereon.

10. An endoscope apparatus having an assembly apparatus, the apparatus comprising:
    an insertion tube having a distal end and a plurality of channels through which endoscopic parts may be disposed, the insertion tube having an outer diameter; and
    an endoscopic assembly disposed on the distal end of the insertion tube, the endoscopic assembly comprising:
       a ligator barrel having proximal and distal portions, the proximal portion having a radially extending seat and a circumferential receiving wall extending to a proximal end, the receiving wall having a first threaded portion formed thereon;
       a gasket having a distal surface disposed on the seat and a radially outer surface disposed on the receiving wall of the ligator barrel and engaging the receiving wall, the gasket having an inner diameter configured to receive the insertion tube; and
       a connector for connecting the ligator barrel about the endoscope, the connector having a scope portion and a tip portion, the scope portion having a receiving end through which the endoscope is disposed to engage the seat for connecting the ligator barrel about the endoscope, the tip portion having a second threaded portion formed thereon, the second threaded portion being configured to cooperate with the first threaded portion to receive the receiving wall and attach the connector with the ligator barrel, the first and second threaded portions being configured to cooperate with each other to tighten the connection of the ligator barrel about the insertion tube as the threads increase surface area contact therebetween, the tip portion further having a tip end abutting the gasket on a proximal surface of the gasket, the connector configured to move longitudinally relative to the insertion tube and to cause the endoscopic assembly to axially compress the gasket between the seat and the tip end during tightening of the connection, thereby reducing the inner diameter of the gasket to press fit onto the endoscope if the outer diameter has any of a plurality of different values that are each within the range of between about 5 to 16 millimeters.

11. The assembly of claim 10 wherein the ligator barrel comprises a stop radially formed therein and extends inwardly, preventing distal advancement of the endoscope relative to the assembly.

12. The assembly of claim 10 wherein the ligator barrel is transparent.

13. The assembly of claim 10 wherein the ligator barrel is made of clear polymer.

14. The assembly of claim 10 wherein the receiving wall comprises an inner surface having the first threaded portion formed thereon.

15. The assembly of claim 10 wherein the tip portion of the connector comprises an outer surface having the second threaded portion formed thereon.

16. The assembly of claim 10 wherein the receiving wall comprises an outer surface having the first threaded portion formed thereon.

17. The assembly of claim 10 wherein the tip portion of the connector comprises an inner surface having the second threaded portion formed thereon.

* * * * *